(12) United States Patent
Krajci

(10) Patent No.: US 6,182,497 B1
(45) Date of Patent: Feb. 6, 2001

(54) GAS DETECTION SYSTEM AND METHOD

(75) Inventor: Juraj Krajci, Coquitlam (CA)

(73) Assignee: Neodym Systems Inc, Vancouver (CA)

( * ) Notice: Under 35 U.S.C. 154(b), the term of this patent shall be extended for 0 days.

(21) Appl. No.: 09/377,417

(22) Filed: Aug. 20, 1999

(51) Int. Cl.$^7$ .......................... G01N 27/00; H04L 12/42; G08C 19/16; G08B 17/00; G08B 26/00

(52) U.S. Cl. .................. 73/23.2; 73/40.5 R; 340/632; 340/605

(58) Field of Search ................ 73/23.2, 40.5 R, 73/40.5 A, 49.1; 340/605, 228, 632, 825.72, 286.02, 856.3, 854.7

(56) References Cited

U.S. PATENT DOCUMENTS

| | | | |
|---|---|---|---|
| 3,726,270 | * | 4/1973 | Griffis et al. ................ 128/2.08 |
| 3,877,291 | * | 4/1975 | Hoppesch et al. ............ 73/27 R |
| 4,173,886 | * | 11/1979 | Archbold et al. ................ 73/23 |
| 4,422,073 | * | 12/1983 | Winner ...................... 340/870.21 |
| 4,517,161 | * | 5/1985 | Gravina et al. ................. 422/95 |
| 4,672,847 | * | 6/1987 | Uchiyama et al. ............... 73/204 |
| 5,025,653 | * | 6/1991 | Schuldt ....................... 73/1 G |
| 5,428,989 | * | 7/1995 | Jerde et al. ................. 73/40.5 R |
| 5,493,272 | * | 2/1996 | Beghelli ....................... 340/505 |
| 5,583,283 | * | 12/1996 | Hampton et al. ............ 73/40.5 R |
| 5,729,207 | * | 3/1998 | Yamano ........................ 340/628 |

FOREIGN PATENT DOCUMENTS

| | | | |
|---|---|---|---|
| 0837328 | * | 4/1998 | (EP) . |
| 2268668 | * | 6/1993 | (GB) . |
| WO92/22813 | * | 6/1991 | (WO) . |

* cited by examiner

*Primary Examiner*—Hezron Williams
*Assistant Examiner*—J. David Wiggins
(74) *Attorney, Agent, or Firm*—Oyen Wiggs Green & Mutala

(57) ABSTRACT

A gas detector system comprises a controller and one or more remote gas sensors. The controller may be a standard personal computer running software for detecting the operational status of the gas sensors and signaling an alarm if the gas sensors indicate an alarm condition. The gas sensors may be connected to the controller by way of a universal serial bus. This architecture provides a gas detection system which can be very flexible and full-featured and yet inexpensive. The gas detectors may include detachable portable units which may be removed from their permanent locations to pinpoint the source of a gas leak or to provide routine monitoring of gas levels. The remote units may include data logging functions so that measurements of gas levels at various locations and times can be stored in the portable units for later transmission back to the controller.

29 Claims, 5 Drawing Sheets

GAS DETECTION SYSTEM AND METHOD

FIELD OF THE INVENTION

This invention relates to gas detection systems. The invention has particular application to systems having multiple gas sensors for detecting hazardous gases at various locations within a facility.

BACKGROUND OF THE INVENTION

There are many situations in which hazardous gases may accumulate in dangerous concentrations. In such cases health and safety regulations and prudence both require a system capable of detecting accumulations of hazardous gases before a hazardous situation exists. For example, many industrial processes use highly flammable or poisonous gases. An industrial plant which uses such processes typically requires a gas detection system having gas sensors distributed throughout the plant and a central station which receives signals from the gas sensors. If one of the gas sensors detects an excessive amount of a hazardous gas then an alarm condition is triggered at the central station.

Such industrial gas detection systems are typically very expensive. The central stations typically include proprietary hardware which has limited upgradability.

Self-contained gas detection systems are also available. A self-contained gas detection system comprises a gas sensor, a battery a simple control circuit and an audible and/or visible alarm contained in a small housing. An example of such self-contained gas detectors are the carbon monoxide detectors and smoke detectors which are widely marketed for use in households and small businesses.

Industrial plants must typically have both built-in gas detection systems and portable self contained gas detectors. If the built-in system detects a troubling amount of a hazardous gas in the vicinity of a particular gas sensor then personnel may be dispatched to the area of the gas sensor in question with portable gas sensors. The portable gas sensors may be used to confirm the amount of hazardous gas detected and to locate the source of the hazardous gas. The management of such industrial plants typically have rigid policies in place which require measurements made by plant personnel to be carefully documented.

Gas sensors are available for detecting a wide range of hazardous gases. Sensors are available for detecting flammable gases, asphyxiating gases of various kinds, radioactive gases, gases containing certain toxins, and so on.

There is a need for a gas detection system which is less expensive to supply and configure than are typical built-in gas detection systems which are now available. There is also a need for gas detection systems which assist in the documentation of gas levels measured with portable gas detectors.

SUMMARY OF THE INVENTION

This invention provides gas detection systems for detecting hazardous gases. The systems use universal serial buses to interconnect gas detectors to a monitoring station.

One aspect of this invention provides a gas detection system for detecting hazardous gases within a facility by way of a number of gas detectors situated at various locations in the facility. The system comprises a monitoring station comprising a programmed computer. The programmed computer comprises a universal serial bus port and a universal serial bus port or hub to which universal serial bus devices can be connected. One or more remote gas detectors are electronically communicating with the monitoring station on a data connection. The data connection has a length exceeding five meters and comprises a universal serial bus and a universal serial bus device. The universal serial bus comprises a universal serial bus cable connected to the universal serial bus port or hub of the computer.

Another aspect of the invention provides a gas detection system comprising: a monitoring station comprising a programmed computer and one or more remote gas detectors electronically communicating with the monitoring station on a data connection. The data connection comprises: a universal serial bus connected to the computer; a protocol converter connected to the universal serial bus; and an electrical cable connecting the protocol converter to the gas detector. Systems according to this aspect of the invention comprise a step-up switching power supply having an input connected to receive electrical power from the universal serial bus and an output connected to provide electrical power to the gas detector by way of electrical conductors in the cable.

A further aspect of the invention provides a gas detection system comprising: a monitoring station comprising a programmed computer, and one or more remote gas detectors electronically communicating with the monitoring station on a data connection, the data connection comprising a universal serial bus connected to the computer. Each of the gas detectors comprises: a portable sensing head and a base. The portable sensing head comprises a hot wire type gas sensor, a gas sensor power supply, a data output, a processor and an audible alarm connected to the processor. The processor is configured to sound the audible alarm when a gas sensor output signal exceeds a threshold value. The base is adapted to detachably hold the portable sensing head and is electronically connected to the monitoring station. The base provides a data connection between the data output and the monitoring station.

A still further aspect of the invention provides a gas detection system for detecting hazardous gases within a facility by way of a number of gas detectors situated at various locations in the facility. The system comprises: a monitoring station comprising a universal serial bus interface, a microcontroller, mini-computer or microprocessor and a universal serial bus port or hub. One or more remote gas detectors electronically communicate with the monitoring station by way of a universal serial bus capable of operating on either a synchronous or asynchronous polling basis. The universal serial bus comprises a universal serial bus cable connected to the universal serial bus port or hub. Each of the remote gas detectors comprises: a portable sensing head comprising a gas sensor, a power supply and a data output; and a base adapted to detachably hold the portable sensing head, the base electronically connected to the monitoring station and providing a data connection between tle data output and the monitoring station.

BRIEF DESCRIPTION OF THE DRAWINGS

In drawings which illustrate specific embodiments of the invention, but which should not be construed as restricting the spirit or scope of the invention in any way.

REFERENCE NUMERALS

| | | | |
|---|---|---|---|
| 10 | gas detection system | 12 | gas detector |
| 14 | monitoring computer | 16 | data link |
| 18 | USB hub | 20 | protocol converter |
| 22 | USB connection | 24 | data connection |
| 26 | data connection | 30 | USB connector |
| 32 | micro controller | 34 | data transceiver |
| 36 | cable connector | 38 | gas detector cable |
| 40 | power supply | 42 | data buffer |
| 44 | power indicator | 46 | USB active indicator |
| 48 | gas detector fault indicator | 50 | base |
| 50A | alternative base | 52 | portable module |
| 52A | tethered module | 53 | step-down voltage regulator |
| 54 | coupler | 56 | gas sensor |
| 58 | sensor support circuitry | 60 | portable power supply |
| 60A | battery | 60B | voltage regulator |
| 60C | charging circuit | 62 | processing circuit |
| 64 | communications circuit | 66 | display |
| 68 | user input | 70 | audio transducer |
| 72 | tag reader | 74 | memory |
| 76 | cable | 77 | signal lights |

DETAILED DESCRIPTION

Figure 1:
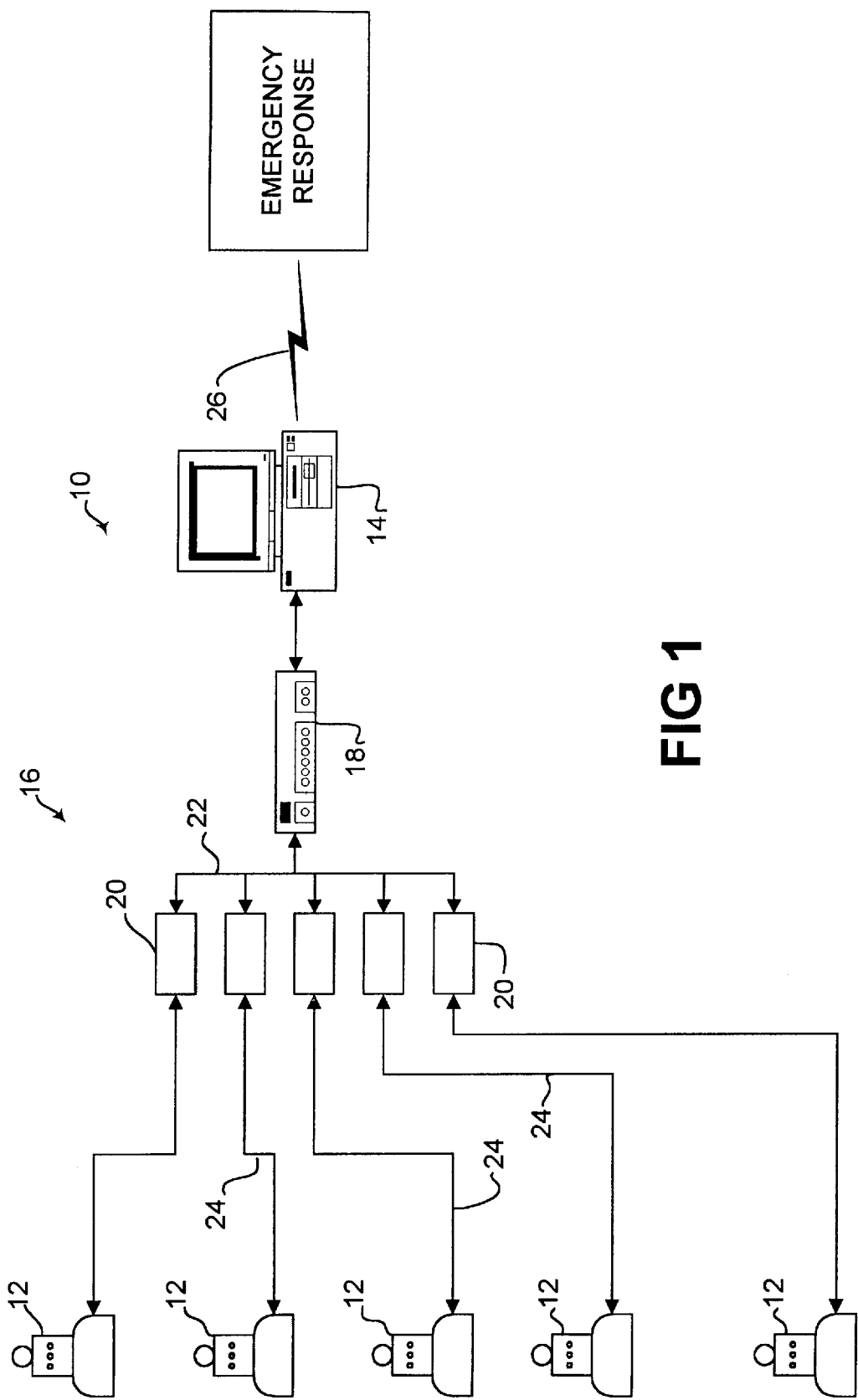
FIG. 1 is a schematic view of a gas detection system according to the invention.

FIG. 1 shows a gas detection system 10 according to a preferred embodiment of the invention. Gas detection system 10 has a plurality of gas detectors 12. Gas detectors 12 are connected to a common monitoring station 14 by a data connection 16. Monitoring station 14 preferably comprises a general purpose personal computer running software which receives data from gas detectors 12 by way of data connection 16. Computer 14 may be connected to one or more remote locations such as an emergency response center, a police department, a fire department, an alarm monitoring center or the like by way of a modem connection or internet connection 26.

Data connection 16 preferably comprises a universal serial bus ("USB") interface in computer 14 connected to a USB hub 18. The USB communication protocol is not reliable over cable runs of longer than about 5 meters. If gas detectors 12 are located more than about 5 meters from computer 14 then data connection 16 comprises a plurality of protocol converters 20. Each protocol converter 20 is a USB device which connects to USB hub 18 with suitable USB wiring. Each protocol converter 20 connects to a gas detector 12 over a communications link 24. Communications link 24 may comprise a wireless communications link such as an infrared link or a radiofrequency link. Preferably communications link 24 comprises a cable on which data can be exchanged between a protocol converter 20 and its corresponding gas detector 12. Most preferably communications link 24 operates according to a protocol which will operate reliably over distances of at least 100 meters. Communications link 24 may, for example, operate according to a protocol such as RS-422 or RS-485.

It can be appreciated that using a standard general purpose computer 14 for a monitoring station avoids much of the cost associated with the development of a monitoring station having a proprietary design. A person generating software for use in monitoring gas detectors 12 can take advantage of the programming tools available for the operating system used by computer 14.

The use of USB to connect data link 16 to computer 14 is advantageous because USB cables and hubs are readily available. Furthermore, the current version of the USB standard allows up to 127 devices to be attached to a single USB port. USB devices can be added to or disconnected from the USB port while computer 14 is running. Thus computer 14 does not need to be restarted to add additional gas detectors 12 to system 10. While one would not normally consider USB for use in interfacing to gas detectors in a gas detection system because of the short (5 meter) cable lengths permitted by the USB protocol this disadvantage can be avoided with the use of a protocol converter according to the invention.

Figure 2:
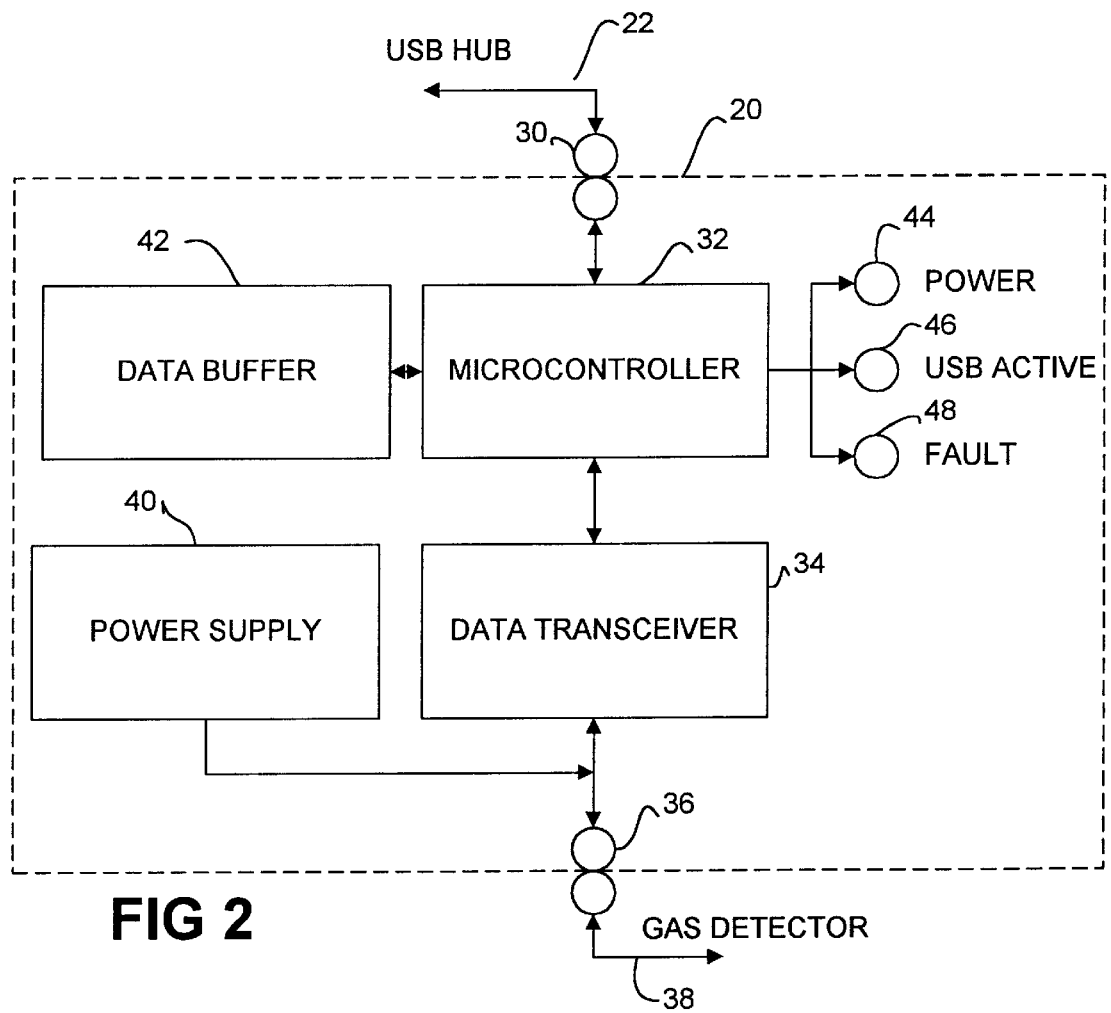
FIG. 2 is a block diagram showing major components of a protocol converter for use in the invention.

FIG. 2 shows a protocol converter 20 according to a preferred embodiment of the invention. Protocol converter 20 has a USB connector 30 for receiving a USB cable 22 connected to a port in computer 14 or a USB hub 18. A micro controller 32 comprising a microprocessor, USB interface engine, timer, program memory is connected to connector 30. A data transceiver 34 is connected to micro controller 32. Data transceiver 34 drives data connection 24. For example, where data connection 24 uses an RS-485 communication protocol then data transceiver 34 may be a RS-485 driver/receiver chip. Data transceiver 34 is connected to a connector 36 which receives a cable 38 connected to a gas detector 12 (unless data connection 24 is a wireless connection).

Micro controller 32 is programmed to receive data from USB connector 30 and forward the data to data transceiver 34 for delivery to gas detector 12. It cannot always be assured that computer 14 will be able to poll gas detector 12 for data and status information as frequently and regularly as would be desired. Therefore, micro controller 32 is preferably programmed to periodically poll gas detector 12 for data and status information by sending a suitable signal to gas detector 12 via data transceiver 34. Most preferably, micro controller 32 polls gas detector 12 on a fully synchronous basis. Micro controller 32 receives data transmitted by gas detector 12 and stores the data in a data buffer 42 until the data is requested by computer 14. Computer 14 can then poll protocol converter 20 on an asynchronous basis with no risk of data loss. Data buffer 42 may be integrated with micro controller 32. By frequently polling gas detector 12, micro controller 32 not only receives up to the second data from gas detector 12 but also continuously verifies that gas detector 12 and communication link 24 are functioning properly. A further advantage of having protocol converter 20 poll gas detector 12 is that bandwidth is conserved on USB 22.

Protocol converter 20 preferably comprises a status indicator. The status indicator of FIG. 2 simply comprises 3 LEDs. LED 44 is illuminated when protocol converter 20 is powered, LED 46 is illuminated when micro controller 32 detects that protocol converter has been properly enumerated by computer 14 as a USB device, and LED 48 is illuminated when proper communications have been established between protocol converter 20 and a gas detector 12. LED 48 may be a bi-color LED which changes color when the gas detector 12 connected to protocol converter signals an alarm condition.

Preferably protocol converters 20 provide electrical power to gas detectors 12 through cables 38. Electrical power may not be conveniently available at the locations of gas detectors 12. Cables 38 may be 4-conductor cables with two conductors being used for simplex data communications between gas detectors 12 and protocol converters 20 and two conductors being used for the power supply.

Since some types of gas detector that may be used in system 10 can draw substantial amounts of electrical current and cables 38 may be very long, there can be a substantial voltage drop on the power carrying conductors of cables 38. This may be dealt with by providing a power supply 40 in protocol converter 20 which supplies power at a higher voltage than the voltage used by gas detectors 12. A voltage regulator in each gas detector 12 can then step down the supply voltage to a voltage suitable for gas detector 12. For example, power supply 40 may be a 12 volt direct current power supply and gas detectors 12 may operate on 5 volts.

Power supply 40 may draw electrical power from USB 22. A USB provides 5 volt electrical power. Where power supply 40 draws power from USB 22 then power supply 40 preferably is a switching power supply which increases the voltage received from USB 22 to a higher voltage as described above. Power supply 40 could, in the alternative be supplied with electrical power from the power mains, from a battery or from some other suitable source of electrical power. Where gas detectors 12 may be operated in explosive environments then power supply 40 is preferably an energy-limited power supply.

Gas detectors 12 may be fixed gas detectors. Gas detectors 12 preferably are capable of operating in both fixed and portable modes. Where gas detectors 12 operate in potentially explosive or flammable environments then they should be constructed in a manner that eliminates the possibility of a spark which could trigger an explosion or fire. Suitable construction techniques are known to those skilled in the field.

Figure 3:
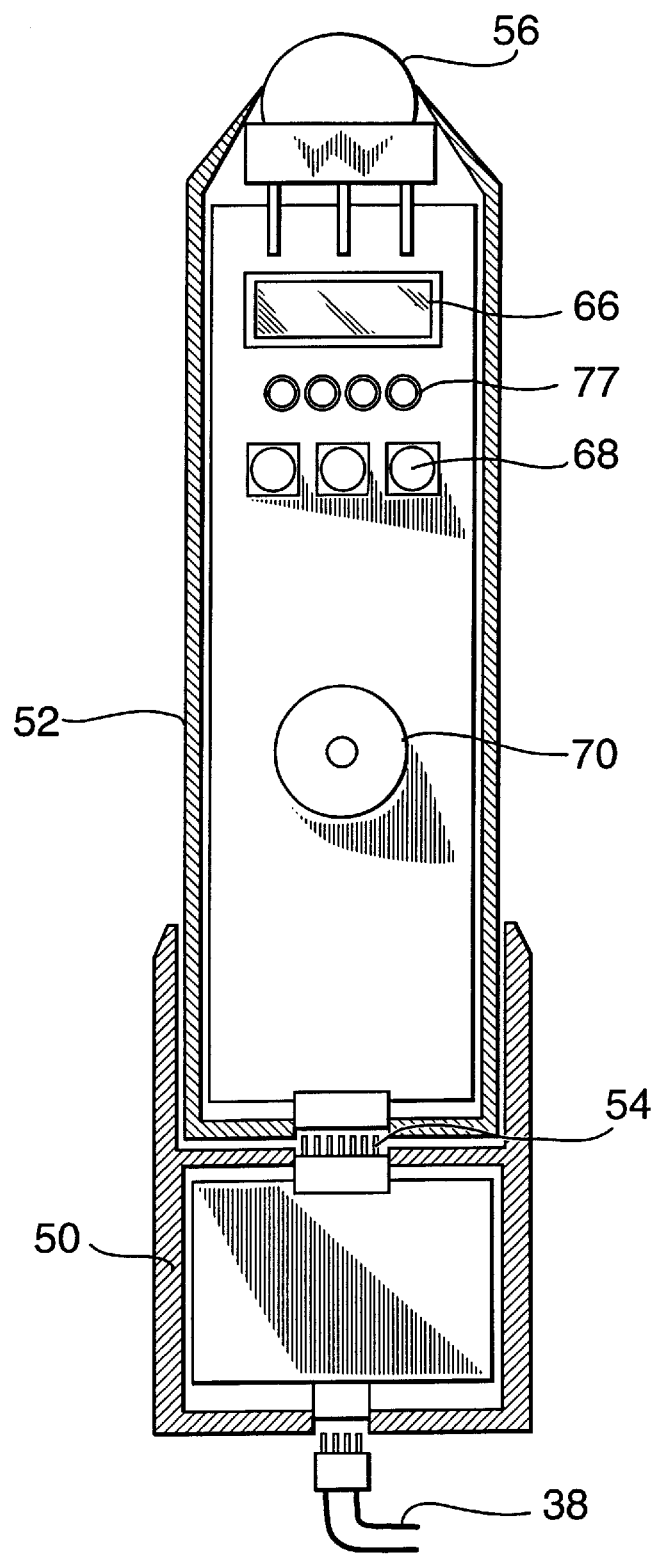
FIG. 3 is a block diagram of a two-part gas detector according to the invention.

As shown in FIG. 3, each gas detector 12 preferably comprises a base 50 and a portable gas sensor module or "sensing head" 52 which is detachably receivable in base 50. Base 50 is mounted in a fixed location and is connected to a protocol converter 20 by cable 38. Base 50 receives data and power from protocol converter 20 over cable 38 and couples data and power to portable module 52. Where power provided by cable 38 is at a higher voltage than the voltage required by portable module 52 then base 50 preferably comprises a voltage regulator 53 mounted on a suitable heat sink.

Gas detectors 12 will typically be at different distances from monitoring computer 14 and cables 38 will consequently be of different lengths. The voltage provided by cables 38 at base 50 will therefore vary depending upon the voltage drop caused by cable 38. Voltage regulator 53 steps down the voltage provided by cable 38 to a value which will be the same for all gas detectors 12 regardless of how far they are from monitoring computer 14. For example, 12 VDC may be provided at the ends of cables 38 away from gas detectors 12 and voltage regulator 53 may have an output of 7.5 VDC.

Base 50 includes an electrical coupler 54 which provides power and data connections to portable module 52. Electrical coupler 54 may comprise an electrical plug, as shown in the drawings, or may, in the alternative, comprise other suitable reliable couplings.

Figure 4:
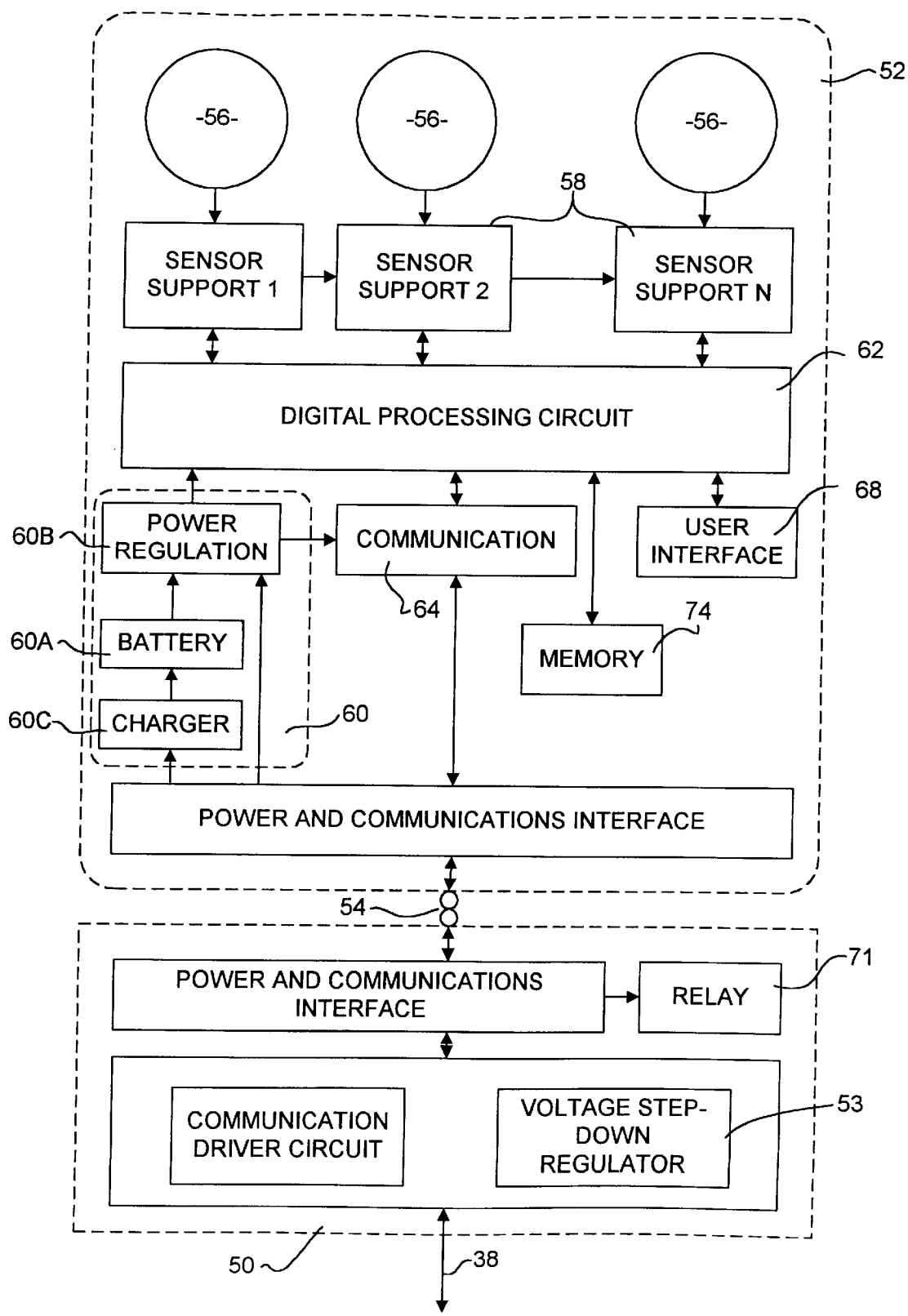
FIG. 4 is a functional block diagram of a gas detector according to the invention; and, FIG. 5 is a functional block diagram of a gas detector according to an alternative embodiment of the invention.

FIG. 4 shows an embodiment of the invention in which the portable unit has several gas sensors. As shown best in FIG. 4, Portable module 52 comprises at least one gas sensor 56. Each gas sensor 56 is supported by a suitable electronic circuit 58. For example, if a gas sensor 56 is a hot wire type of gas sensor then circuit 58 will provide the electrical circuitry necessary to generate an electrical current through the hot wire and to measure the voltage drop across the hot wire. Different types of gas sensor require different types of support circuitry as is known in the art. A portable module 52 may have several different types of gas sensor 56. Gas sensors 56 may include sensors for combustible gases, sensors for toxic gases, sensors for smoke, sensors for bio-hazards or the like.

Portable module 52 is self powered by a power supply 60 such as a rechargeable battery, long life disposable batteries or the like. The output voltage of a rechargeable battery can vary significantly as the battery discharges. Since the electronic circuitry of module 52 operates most consistently when powered by a precisely regulated constant voltage, power supply 60 of module 52 preferably comprises a long life rechargeable battery 60A, a second voltage regulator 60B and a battery charger 60C. Voltage regulator 60B steps down the voltage of battery 60A to a steady level, for example 5 VDC, which powers portable module 52. Since the output of voltage regulator 53 is greater than the voltage of battery 60A, battery 60A can be charged by charger 60C when portable unit 52 is plugged into base 50. Voltage regulator 60B provides a constant voltage supply for the electronic circuitry of portable module 52 whether or not module 52 is plugged into base 50.

A digital processing circuit 62 which preferably comprises a microprocessor, program memory, data memory, and a timer monitors the outputs from sensors 56. When portable module 52 is plugged into base 50 then portable module 52 is frequently polled by protocol converter 20. In response, digital processing circuit 62 transmits readings from sensors 56 and information regarding the operational status of portable module 52. A digital communications circuit 64 receives data sent over cable 38 by protocol converter 20 and sends data generated by digital processing circuit 62 to protocol converter 20.

Processing circuit 62 preferably compares the readings from sensors 56 with pre-set alarm limits. If the readings indicate gas concentrations in excess of the alarm limits then processing circuit 62 preferably triggers a local alarm. The alarm may comprise, for example, flashing a strobe light 77 on gas detector 12 and/or sounding an audible alarm.

If power supply 60 comprises a rechargeable battery then the battery is charged when portable unit 52 is plugged into base 50. When portable module 52 is removed from base 50 then portable unit 52 operates in stand-alone mode under power supplied by power supply 60. As shown in FIG. 3, portable unit 52 preferably comprises a display 66, a user input 68 connected to processor 62, an audio transducer 70, and a tag reader 72. While in stand alone mode an operator can move portable module 52 from place to place in an attempt to localize the source of detected gases. Visual and audible signals may be generated by processor 62 via display 66 and audible signal 70 to provide the operator with feedback regarding the amount of gas being detected by sensors 56.

A relay 71 controlled by processor 62 is located in base 50. When portable module 52 is connected to base 50, processor 62 may activate relay 71 when an alarm condition is detected. Relay 71 may switch local loads such as gas shut-off valves, area sirens, strobe lights, ventilation fans, etc.

Portable unit 52 preferably comprises a data logger. The data logger may be implemented in digital processing circuit 62 by providing a memory 74 into which digital processing circuit 62 can store data regarding readings made by gas sensor(s) 56 together with information identifying the times and places at which such readings were made. Memory 74 is preferably a non-volatile memory so that data will not be lost if power supply 60 fails. Memory 74 and digital processing circuit 62 may conveniently be integrated on one chip.

In one embodiment of the invention machine readable tags are located at points where it may be desired to take readings of gas concentrations. The tags may be, for example, bar coded tags, magnetically coded tags, or other machine readable tags. A user can read the tags with tag reader 72. Processing circuit 62 records tag identification information from tag reader 72, time information from a clock in processing circuit 62 and gas concentration information, as measured by sensors 56 in memory 74. After one or more measurements have been made then portable unit 52 can be placed back into base 50 and the data accumulated in memory 74 can be carried to central station 14 on data connection 16.

Figure 5:
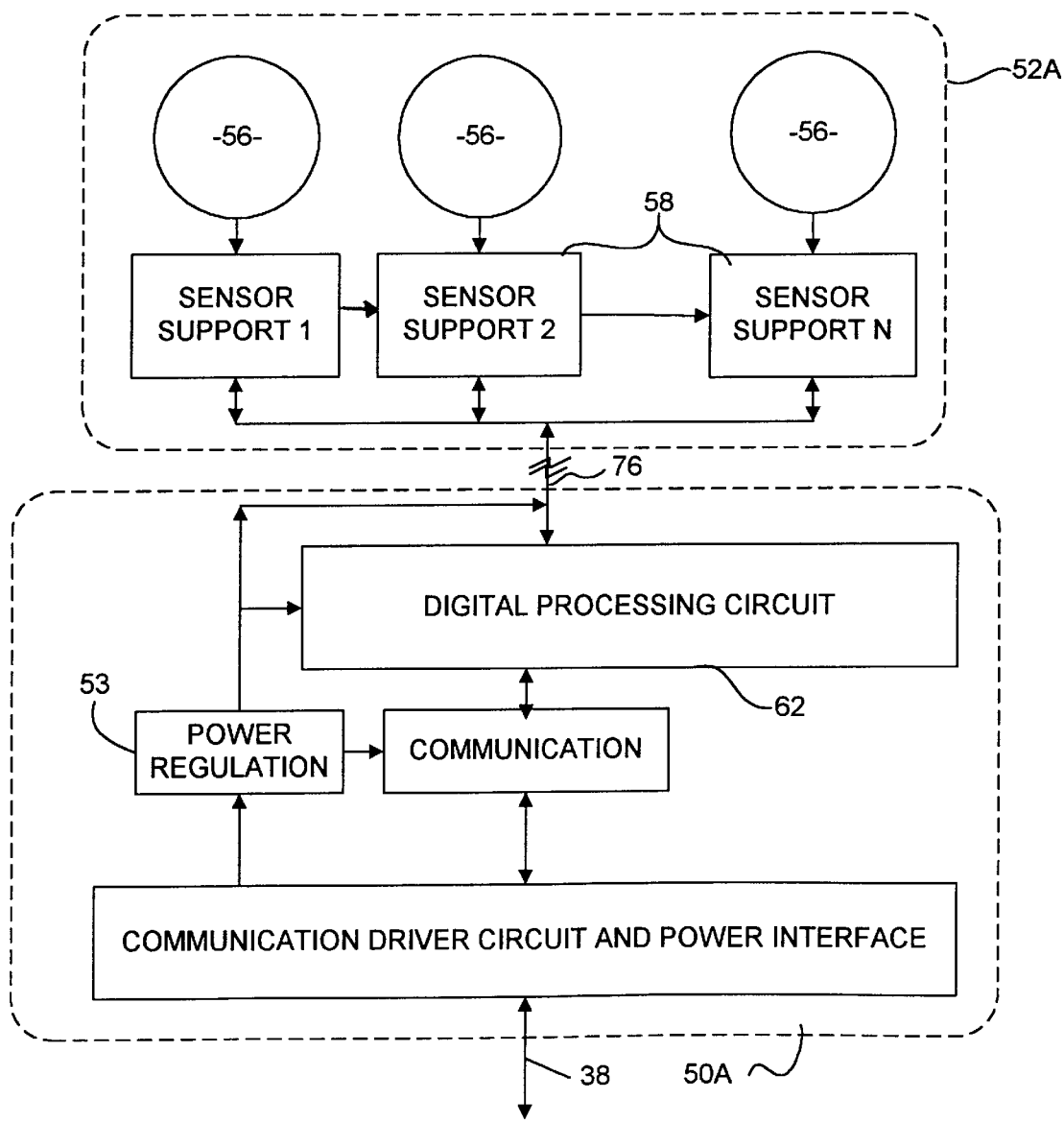

In an alternative embodiment of the invention, as shown in FIG. 5, portable unit 52A remains connected to base 50A by a cable 76 at all times. Portable unit 52A is normally held in place on base 50A but can be removed from base 50A and moved to various adjacent locations. Cable 76 is long enough to allow portable unit 52A to extend to such locations. Cable 76 might, for example be 10 meters or less in length.

Display 66 may be capable of displaying alphanumeric information generated by processing circuit 62 or central station 14. For example, central station 14 may convey text messages to a user via data connection 16. The text messages might instruct the user to proceed to a certain test point and take a gas concentration reading there. Processing circuit 62 receives the text messages and causes them to be displayed on display 66.

The system of the invention makes possible a method for monitoring for and responding to alarm conditions, such as excessive concentrations of hazardous gases. A facility to be protected by a system according to the invention is provided with one or more gas detectors 12 at selected locations. The gas detectors 12 are in data communication with a central station 14. Software running on central station 14 remotely monitors the gas levels detected by gas detectors 12. In each gas detector, an electrical signal output from each gas sensor is measured and compared to a preset reference value. Each gas detector transmits its information to central station 14. If the detected signal value at a gas detector 12 equals or exceeds the reference value (i.e. if an alarm condition exists), then processor 62 in the gas detector 12 activates the detector's local signal lamps 77, audio transducer, and relay 71, and displays details of the alarm event on its display 66. A message containing the event information is also transmitted to central station 14 where it can be displayed and acted upon by response. personnel. Central station 14 may also broadcast details of the alarm condition to a remote site by way of an internet connection or some other communications link.

When the alarm condition has been detected then a human investigator may be sent to the alarm zone. The investigator may wish to isolate the source of the problem. The investigator may remove portable module 52 from its base 50 and perform a series of measurements using the portable module 52 as a portable monitoring instrument. The investigator may have a procedure that entails acquiring readings at predetermined locations to discover the source or cause of the alarm event. In that mode of operation, the alarm lamps, audio transducer and display read-out of the detector respond in real-time to the sensory input and can be used to narrow in on the precise location of the cause of the alarm condition.

As each reading is performed, the investigator pushes a button 68 on portable module 52 and records in memory 74 the location, time and physical parameters of the reading. The location may be noted, for example, by entering a location code on a keypad or other data entry button on portable module 52, or scanning a bar code, or other machine-readable tag identifying the location with a tag reader 72 on portable module 52. In the alternative, a predefined list of locations could be stored in memory in portable module 52. The operator may locate the current location by, for example, scrolling through the list of predefined locations. Where a predefined list of locations is stored in module 52, module 52 may also be programmed to assume that the locations will be visited in a set order. When a first measurement is taken, module 52 will associate that first measurement with a first location in the list, when a second measurement is taken, module 52 will associate the result of the second measurement with a second location in the list, and so on. If the user makes a sequence error or wishes to repeat a sample then module 52 may permit the user to scroll through the list of locations as described above.

Upon completion of the investigation procedure, the operator returns the portable module 52 to its base 50 whereupon the portable module 52 uploads the captured data to the central station 14 where it can be analysed, archived and formatted for reports.

As will be apparent to those skilled in the art in the light of the foregoing disclosure, many alterations and modifications are possible in the practice of this invention without departing from the spirit or scope thereof. For example, while the invention is described as using microprocessors to coordinate the operation of protocol converters 20 and portable modules 52, application-specific integrated circuits could be used instead. While the invention has been described as including sensors for hazardous gases, the term gases should be interpreted expansively to include any potentially hazardous airborne material for which a sensor can be provided. For example, the invention could be used to detect smoke or certain bio-hazardous materials in addition to things more conventionally described as gases. Accordingly, the scope of the invention is to be construed in accordance with the substance defined by the following claims.

I claim:

1. A gas detection system for detecting hazardous gases within a facility by way of a number of gas detectors situated at various locations in the facility, the system comprising:

a) a monitoring station comprising a programmed computer having a universal serial bus interface, the programmed computer comprising a universal serial bus port or hub;

b) one or more remote gas detectors electronically communicating with the monitoring station on a data connection, the data connection having a length exceeding five meters and comprising: a universal serial bus, the universal serial bus comprising a universal serial bus cable connected to the universal serial bus port or hub of the computer; and, a universal serial bus device.

2. The gas detection system of claim 1 wherein the universal serial bus device comprises a protocol converter connected to the universal serial bus cable; and, the data connection for one or more of the gas detectors comprises an electrical cable connecting the protocol converter to the gas detector.

3. The gas detection system of claim 2 wherein the protocol converter comprises a universal serial bus device controller connected to the universal serial bus and a line driver connected to the cable.

4. The gas detection system of claim 3 wherein the protocol converter comprises a data buffer connected between the line driver and the universal serial bus device controller, the data buffer receiving from the line driver data received from the gas detector and forwarding the data to the universal serial bus device controller.

5. The gas detection system of claim 4 wherein the line driver communicates with the gas detector using a RS-422 protocol.

6. The gas detection system of claim 4 wherein the line driver communicates with the gas detector using a RS-485 protocol.

7. The gas detection system of claim 2 wherein the protocol converter comprises a power supply connected to provide electrical power to the gas detector by way of electrical conductors in the cable.

8. A gas detection system comprising:
 a) a monitoring station comprising a programmed computer;
 b) one or more remote gas detectors electronically communicating with the monitoring station on a data connection, the data connection comprising:
  i) a universal serial bus connected to the computer;
  ii) a protocol converter connected to the universal serial bus;
  iii) an electrical cable connecting the protocol converter to the gas detector; and
 c) a step-up switching power supply having an input connected to receive electrical power from the universal serial bus and an output connected to provide electrical power to the gas detector by way of electrical conductors in the cable.

9. The gas detection system of claim 1 wherein each of the remote gas detectors comprises:
 a) a portable sensing head comprising a gas sensor, a gas sensor power supply and a data output; and,
 b) a base adapted to detachably hold the portable sensing head, the base electronically connected to the monitoring station and providing a data connection between the data output and the monitoring station.

10. The gas detection system of claim 9 wherein the gas sensor power supply comprises a rechargeable battery.

11. The gas detection system of claim 10 wherein the base comprises a battery charger and, when the sensing head is held in the base, the battery charger is connected to the rechargeable battery.

12. The gas detection system of claim 9 wherein the sensing head comprises a processor and an audible alarm connected to the processor, the processor configured to sound the audible alarm when a gas sensor output signal exceeds a threshold value.

13. A gas detection system comprising:
 a) a monitoring station comprising a programmed computer; and
 b) one or more remote gas detectors electronically communicating with the monitoring station on a data connection, the data connection comprising a universal serial bus connected to the computer, wherein each of the gas detectors comprises:
  i) a portable sensing head comprising a hot wire type gas sensor, a gas sensor power supply, a data output, a processor and an audible alarm connected to the processor, the processor configured to sound the audible alarm when a gas sensor output signal exceeds a threshold value; and
  ii) a base adapted to detachably hold the portable sensing head, the base electronically connected to the monitoring station and providing a data connection between the data output and the monitoring station.

14. The gas detection system of claim 9 wherein the portable sensing head comprises a plurality of gas sensors.

15. The gas detection system of claim 9 wherein the sensing head comprises a data logger connected to log an output signal of the gas sensor.

16. The gas detection system of claim 12 wherein the sensing head comprises a data reader connected to the data logger, the data logger configured to log data from the data reader and the output signal of the gas sensor.

17. The gas detection system of claim 16 wherein the processor comprises a timer and the data logger is configured to log a time at which the output signal of the gas sensor is measured together with the output signal of the gas sensor.

18. The gas detection system of claim 1 wherein the data connection for one or more of the gas detectors comprises:
 a) a universal serial bus connected to the computer;
 b) a protocol converter connected to the universal serial bus; and,
 c) a wireless data connection connecting the protocol converter to the gas detector.

19. The gas detection system of claim 18 wherein the wireless data connection comprises a radiofrequency data link.

20. The gas detection system of claim 18 wherein the wireless data connection comprises an infrared link.

21. The gas detection system of claim 13 wherein the data connection comprises:
 a) a protocol converter connected to the universal serial bus; and
 b) an electrical cable connecting the protocol converter to the gas detector.

22. The gas detection system of claim 21 wherein the protocol converter comprises a universal serial bus device controller connected to the universal serial bus and a line driver connected to the cable.

23. The gas detection system of claim 22 wherein the protocol converter comprises a data buffer connected between the line driver and the universal serial bus device controller, the data buffer receiving from the line driver data received from the gas detector and forwarding the data to the universal serial bus device controller.

24. The gas detection system of claim 13 wherein the sensing head comprises a data reader connected to the data logger, the data logger configured to log data from the data reader and the output signal of the gas sensor.

25. The gas detection system of claim 24 wherein the processor comprises a timer and the data logger is configured to log a time at which the output signal of the gas sensor is measured together with the output signal of the gas sensor.

26. A gas detection system for detecting hazardous gases within a facility by way of a number of gas detectors situated at various locations in the facility, the system comprising:

a) a monitoring station comprising a universal serial bus interface, a universal serial bus port or hub and a microcontroller, mini-computer or microprocessor connected to receive data by way of the universal serial bus port or hub;

b) one or more remote gas detectors electronically communicating with the monitoring station by way of a universal serial bus capable of operating on either a synchronous or asynchronous polling basis, the universal serial bus comprising a universal serial bus cable connected to the universal serial bus port, each of the remote gas detectors comprising:
  i) a portable sensing head comprising a gas sensor, a power supply and a data output;
  ii) a base adapted to detachably hold the portable sensing head, the base electronically connected to the monitoring station and providing a data connection between the data output and the monitoring station.

27. The monitoring system of claim 26 wherein the power supply in the portable sensing head comprises a rechargeable battery.

28. The monitoring system of claim 27 wherein the base is connected to the monitoring station by a data connection comprising a cable and electrical power is supplied to the base through the cable.

29. The monitoring system of claim 28 comprising a voltage regulator in the base, the voltage regulator receiving electrical current at a first voltage from the cable and providing electrical current at a second voltage lower than the first voltage to the portable sensing head.

* * * * *